(12) United States Patent
Al-Jazaeri (10) Patent No.: US 12,274,798 B2
(45) Date of Patent: Apr. 15, 2025

(54) NON-CONTACT FLUID DISPENSER

(71) Applicant: KING SAUD UNIVERSITY, Riyadh (SA)

(72) Inventor: Ayman Hassan Al-Jazaeri, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 905 days.

(21) Appl. No.: 17/239,657

(22) Filed: Apr. 25, 2021

(65) Prior Publication Data

US 2022/0001045 A1 Jan. 6, 2022

Related U.S. Application Data (60) Provisional application No. 63/048,517, filed on Jul. 6, 2020.

(51) Int. Cl.
*A61L 2/00* (2006.01)
*A47K 5/12* (2006.01)

(52) U.S. Cl.
CPC .......... *A61L 2/0088* (2013.01); *A47K 5/1201* (2013.01); *A61L 2202/15* (2013.01); *A61L 2202/16* (2013.01)

(58) Field of Classification Search
CPC .......................... A61L 2202/16; A61L 2202/15
See application file for complete search history.

(56) References Cited

U.S. PATENT DOCUMENTS

| 5,292,031 A | * | 3/1994 | Dagan | A61L 12/086 |
| | | | | 222/105 |
| 2011/0182652 A1 | * | 7/2011 | Chung | A61L 2/18 |
| | | | | 401/218 |
| 2018/0235441 A1 | * | 8/2018 | Huang | A61B 1/015 |

FOREIGN PATENT DOCUMENTS

| EP | 3017884 A1 * | 5/2016 | ............. A47L 11/34 |
| EP | 3061374 A1 * | 8/2016 | ........... A47K 5/1201 |
| KR | 20200062966 A * | 6/2020 | ............. F24F 13/02 |
| WO | WO-2017019722 A1 * | 2/2017 | ............. A47L 13/19 |

OTHER PUBLICATIONS

KR_20200062966_A_Translation (Year: 2020).*
Valin Corporation, "Igenix Pinch Valves", May 7, 2014, Youtube, https://www.youtube.com/watch?v=1UKAnNXAEcU (Year: 2014).*

* cited by examiner

*Primary Examiner* — Kevin Joyner
*Assistant Examiner* — Changru Chen
(74) *Attorney, Agent, or Firm* — Nath, Goldberg & Meyer; Joshua B. Goldberg (57) ABSTRACT

A wearable non-contact fluid dispenser is provided. An arm band fastened to a user's arm having receptacle configured to hold a compressible pouch, the pouch retaining a volume of sanitation fluid. A flexible elastic tube extends from the pouch to an outlet positioned approximately to the user's palm. A hands-free valve may release sanitation fluid from the pouch to the user's palm enabling the user to sanitize their hands. The flow rate of the sanitation fluid may be controlled by the user.

15 Claims, 5 Drawing Sheets

NON-CONTACT FLUID DISPENSER

CROSS-REFERENCE TO RELATED APPLICATIONS

The present application claims priority to U.S. Provisional Application Ser. No. 63/048,517 filed on Jul. 6, 2020 entitled "Touchless Wearable Antiseptic Fluid Dispenser", the disclosure of which is hereby incorporated in its entirety at least by reference.

BACKGROUND OF THE INVENTION

1. Field of the Invention

The present invention generally relates to fluid dispensers and more particularly to a non-contact fluid dispenser wearable by a user.

2. Description of Related Art

Many infectious agents or germs are transmitted via hand contact such as the viruses responsible for influenzas infection including the corona virus responsible for the COVID-19 pandemic. Frequent cleanliness and sanitation of a person's hands is critical for preventing the spread of the infectious agents. Without access or time to visit a sink for hand washing procedures, portable alcohol-based sanitation has become a more accessible alternative. Wall-mounted, pocket and table-top sanitation containers and sprays are the most common forms of hand sanitizers. However, in situations where frequent sanitation is necessary, these solutions are blundersome and hard to use repetitively while performing multiple tasks. For instance, wall-mounted sanitizer requires frequent maintenance and refill otherwise they become a focus for spreading infections as multiple user touch the empty dispenser with their contaminated hands without dispensing any sanitizing agents. Pocket containers and sprays has to be picked-up from the pocket which can potentially contaminate the pockets and its other contents. Table-top dispenser are not frequently available, can be displaced and the quality of contents might not be always reliable. We are proposing a design for a wearable device that can dispense sanitizing fluid or any other fluid without hand touch, potentially eliminating the risk of hand contamination during hand sanitization.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

It is an object of the invention to provide a device that dispenses a sanitization fluid into the palm of a user. It is another object of the invention to provide a hands-free dispenser of fluid.

In order to do so a non-contact fluid dispenser is provided, the dispenser comprising a compressible container configured to hold a volume of fluid; a conduit having a first end and a second end, the first end in fluid communication with the volume of fluid, wherein the second end is in fluid communication with an outlet; a valve configured to release fluid from the volume of fluid through the conduit, wherein the valve is operable without the use of a hand of a user; and, wherein the non-contact fluid dispenser is configured to be fastened to the user's arm.

In one embodiment, the volume of fluid is sanitation liquid configured to be dispensed into a hand of the user. In one embodiment, the compressible container is a disposable pouch. In one embodiment, the compressible container is configured to be removably housed in an inner volume of a receptacle. In another embodiment, the receptacle is attached to an arm strap configured to be fastened around an arm of the user. In another embodiment, the valve is removably fastened to an outer surface of the receptacle or the arm strap. In another embodiment, the compressible container is configured to compress via a pressure applied to the receptacle. In yet another embodiment, the pressure applied is via tension wires adjustable via a pressure adjustment knob. In another embodiment, the compressible container is configured to be compressed manually with an elastic zipper of the receptacle in the arm strap. In another embodiment, the compressible container is configured to be compressed manually with an inflatable pneumatic pouch integrated within the receptacle.

In one embodiment, the valve is a pinch-type momentary control valve in a normally closed position operable by the variable depression of a button. In one embodiment, in a first mode of operation, the button of the valve is configured to be depressed between the medial aspect of an upper position on an arm and a lateral aspect of a chest wall of the user. In one embodiment, the conduit is a flexible elastic tube having an adjustable length. In another embodiment, the outlet is positioned approximately at a palm of the hand. In another embodiment, the non-contact fluid dispenser is at least one of: a forearm and wrist strap configured to hold and guide the conduit to the palm of the hand. In one embodiment, the compressible container includes a leak-proof cap, wherein the first end of the conduit is received by the cap. In another embodiment, the receptacle has a first opening enabling the removal of the compressible container such that a new compressible container may be installed, wherein the first opening is reversibly closable via a fastener. In yet another embodiment, the receptacle has a second opening configured to enable the conduit to enter the inner volume of the receptacle.

In another aspect of the invention, a wearable non-contact fluid dispenser is provided, the dispenser comprising an arm band attached to a compressible receptacle, wherein the arm band is configured to be fastened to a user's arm; a compressible pouch configured to hold a volume of sanitation fluid housed in the compressible receptacle; a flexible elastic tube having a first end and a second end, the first end is in fluid communication with the volume of sanitation fluid, wherein the second end forms an outlet, and the outlet is positioned approximately to the user's palm; and, a valve configured to release sanitation fluid from the compressible pouch through the flexible elastic tube into the user's palm, wherein the valve is operable via arm movement without the use the user's hands.

In another aspect of the invention, a method of dispensing sanitation fluid without the use of hands is provided, the method comprising steps: (a) providing a wearable non-contact fluid dispenser comprising a compressible container configured to hold the sanitation fluid, a tube in fluid communication with the sanitation fluid, and a valve configured to control the flow of the sanitation fluid through the tube; (b) fastening the wearable non-contact fluid dispenser to an arm of a user; (c) arranging the tube such that an outlet portion of the tube is positioned approximately to a palm of the user; and, (d) activating the valve via a pressing force between the arm and a body of the user such that the sanitation fluid is dispensed into the palm of the user.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims

BRIEF DESCRIPTION OF THE SEVERAL VIEWS OF THE DRAWINGS

Other features and advantages of the present invention will become apparent when the following detailed description is read in conjunction with the accompanying drawings, in which:

FIG. 8 is a top view of the non-contact fluid dispenser with the bottle out of the receptacle according to an embodiment of the present invention;

DETAILED DESCRIPTION OF THE PREFERRED EMBODIMENT

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide a non-contact fluid dispenser wearable by a user.

The word "a" is defined to mean "at least one." As used in this application, the term "about" or "approximately" refers to a range of values within plus or minus 20% of the specified number or position. Unless otherwise defined, all technical terms used herein have the same meaning as commonly understood by one of ordinary skill in the art to which this disclosure belongs.

Figure 1:
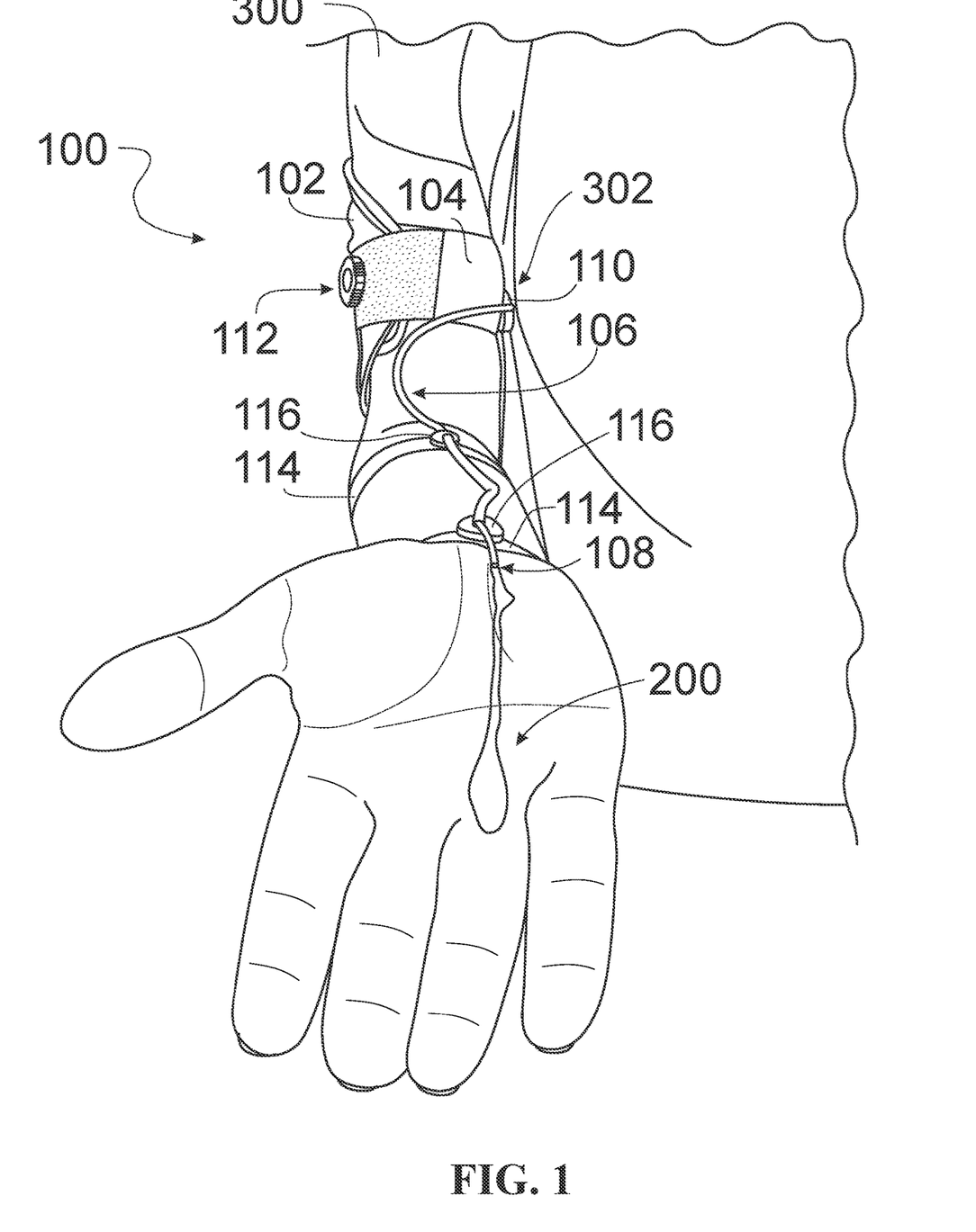
FIG. 1 is a perspective view of a non-contact fluid dispenser wearable by a user in use according to an embodiment of the present invention.
Figure 2:
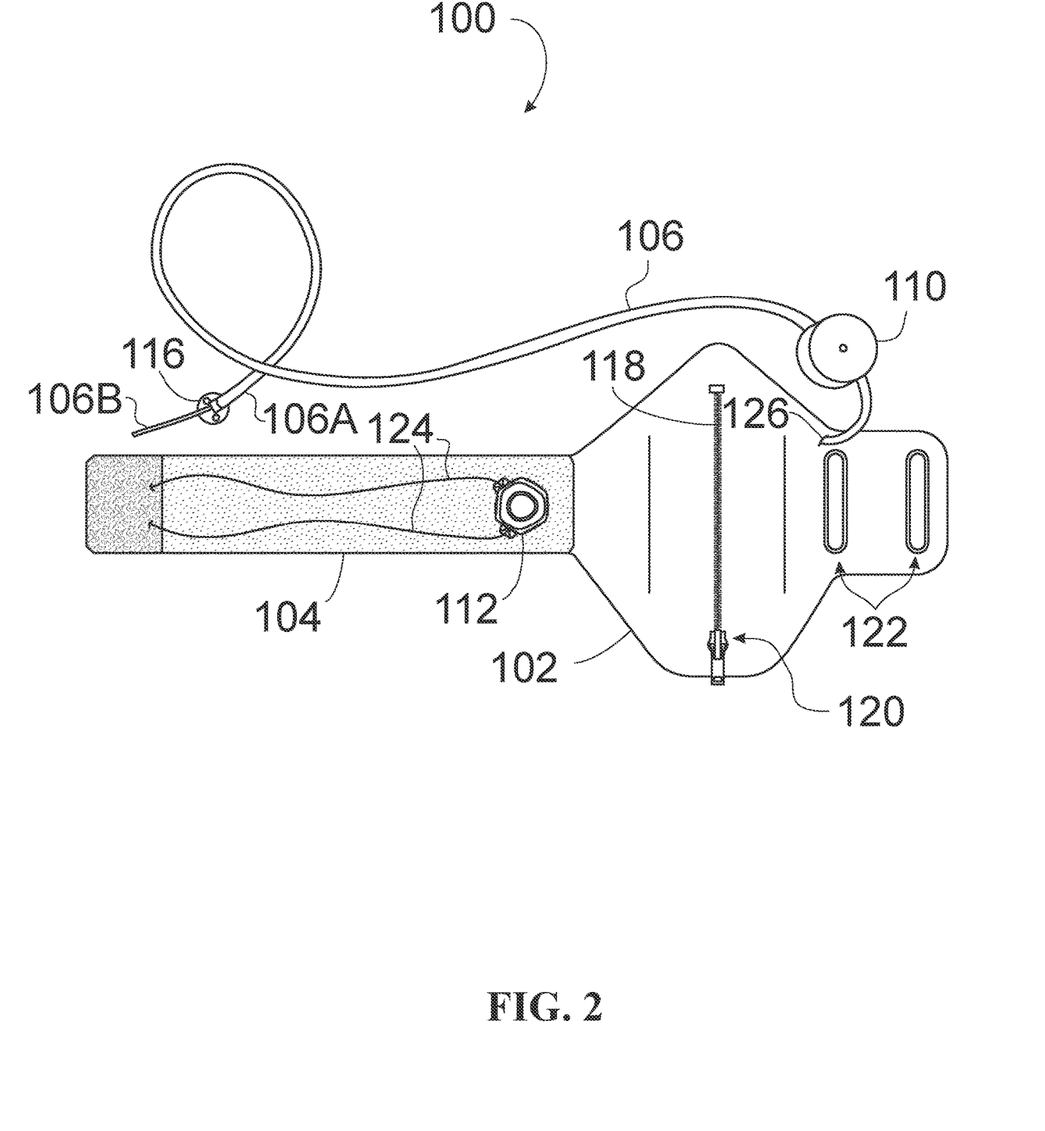
FIG. 2 is a top view of the non-contact fluid dispenser according to an embodiment of the present invention.
Figure 3:
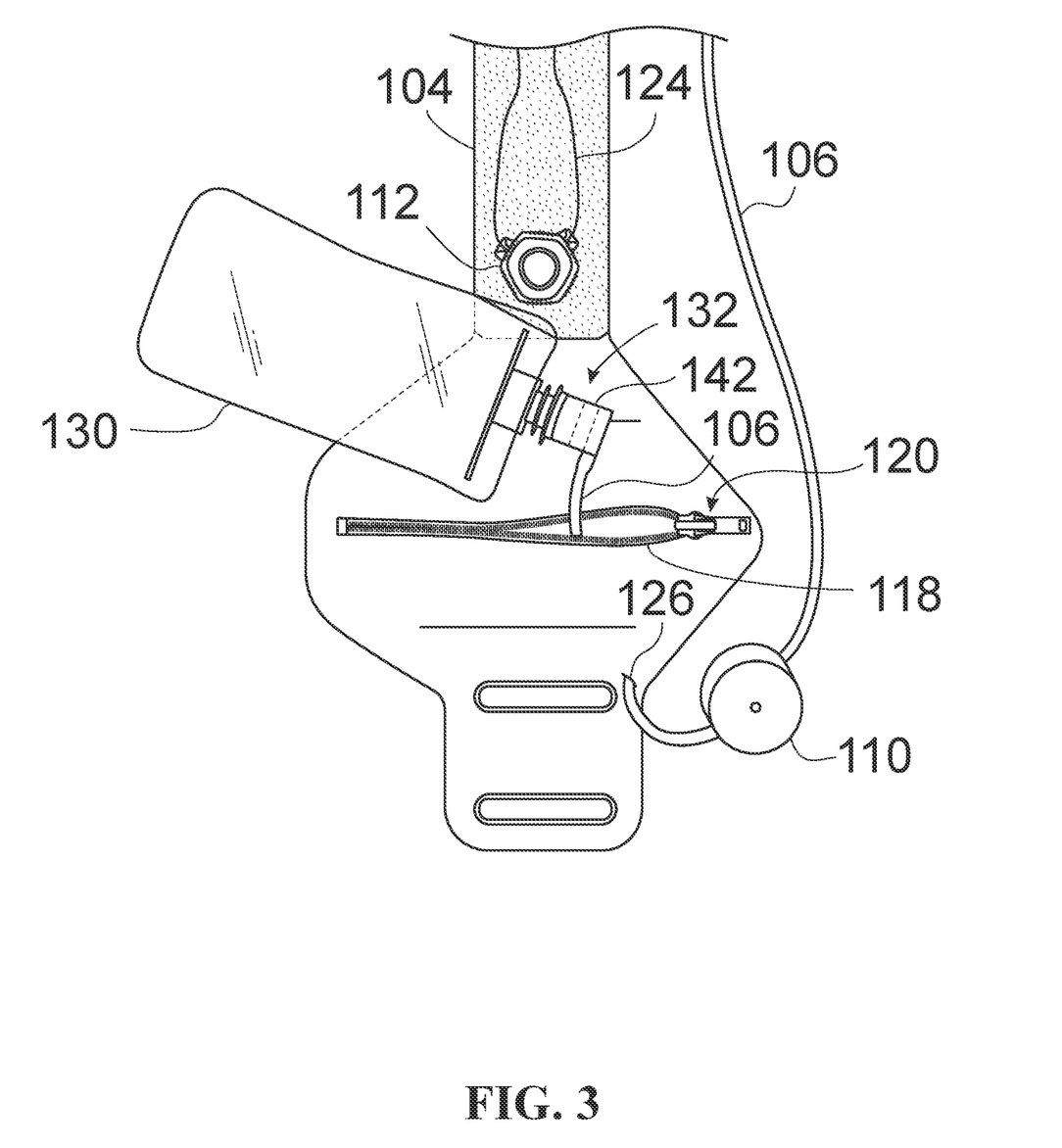

Referring now to FIGS. 1-3, a non-contact fluid dispenser 100 wearable by a user is illustrated. In one embodiment, the non-contact fluid dispenser 100 comprises a compressible receptacle 102 attached to an arm band 104, wherein the arm band is configured to be fastened to a user's arm 300. In one embodiment, a compressible pouch 130 is housed in the receptacle 102, wherein the compressible pouch 130 is configured to hold a volume of sanitation fluid. The volume of sanitation fluid is configured to be any gel or liquid that contains a composition of at least one sanitation ingredient as well known in the art, such as alcohol at a predetermined percentage. It should be understood, that any sanitation fluid may be used in the present invention. Likewise, any fluid may be used in the dispenser of the present invention. In some embodiments, the compressible pouch 130 is accessible in the receptacle 102 via a first opening 126. A fastening means, such as zipper 120, is configured to reversibly close the first opening 126 to secure and access the compressible pouch 130 as needed. In some embodiments, the compressible pouch 130 is configured to be removed and discarded after the volume of sanitation has been used. In alternative embodiments, the compressible pouch 130 is adapted to be reusable. The compressible pouch may be a bottle, container, etc. in which the inner volume of the pouch may be reduced via compression. Although having a compressible pouch, bottle, or container is required for the embodiment described in the present invention, it should be understood that a non-compressible container may work if certain pressure conditions are met. This will be explained in greater detail below.

In some embodiments, the compressible pouch 130 includes a cap 132, wherein the cap 132 is a screw operated (as illustrated) or a pressure fit (pull-off) cap. A connecting nipple is configured to receive one end of a tube 106, such that the tube 106 is in fluid communication with the volume of sanitation fluid. In some embodiments, the cap may include an O-ring 142 to prevent leaking by forming a hermetic seal. The tube 106 may be constructed from any material, but preferably should be elastic. In one embodiment, the tube 106 has an outer diameter of 4 mm and an inner diameter of 2 mm however, it should be understood these dimensions may vary. The diameter of the tube 106 is selected for its compatibility with other components such as the cap 132 and valve 110 as well as the indented flow rate of the sanitation fluid during use, which is also adjustable by the present invention. Best seen in FIG. 1, during use, the valve 110 is configured to release sanitation fluid 200 from the compressible pouch 130 through the tube 106 into the user's palm.

Figure 4:
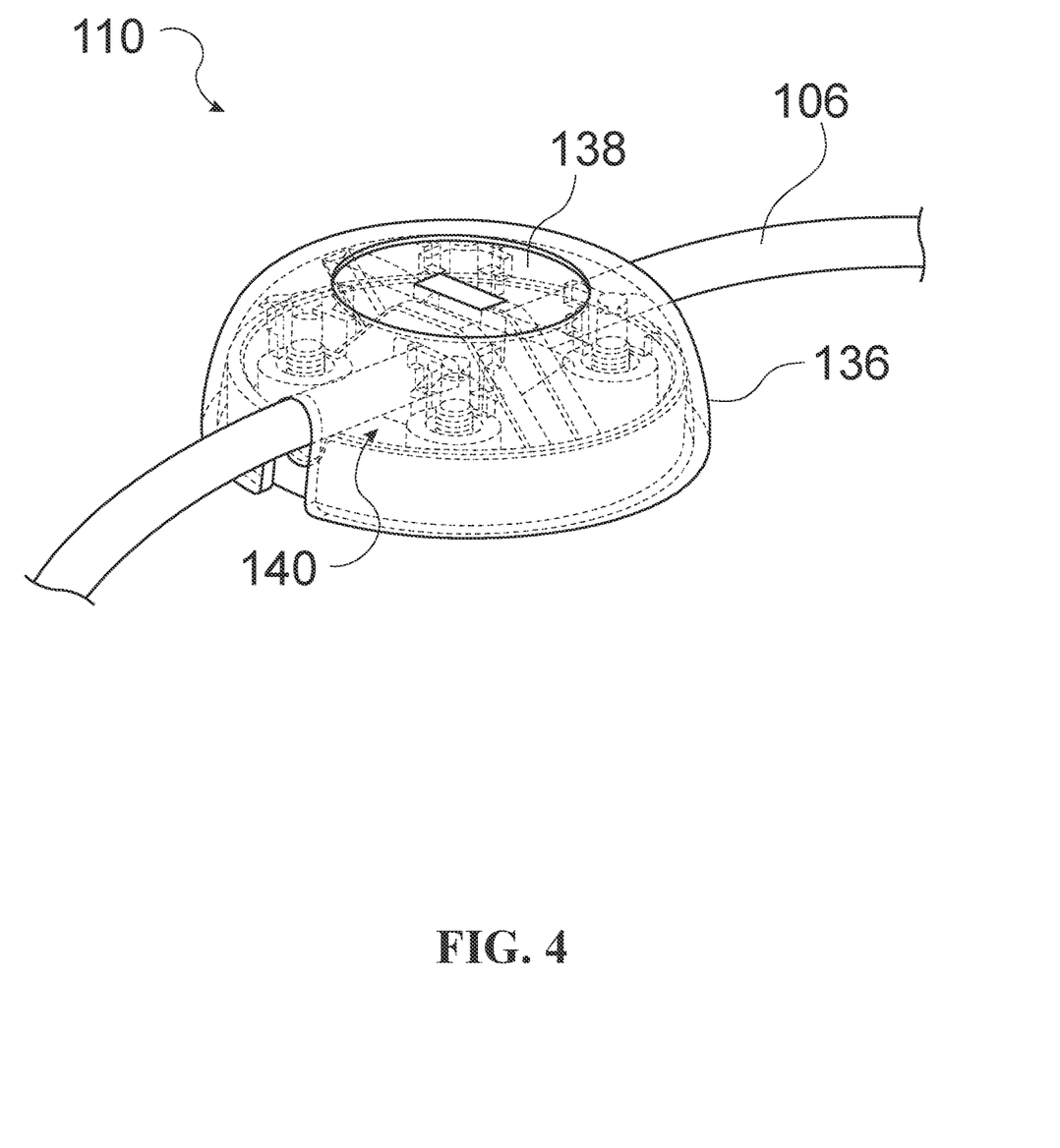
FIG. 4 is a detailed view of the valve according to an embodiment of the present invention; and, FIG. 5 is a detailed view showing a pressure adjustment mechanism in use the according to an embodiment of the present invention.

Referring now to FIG. 4, a detailed view of the valve 110 is illustrated. In one embodiment, the valve is a pinch-type momentary control valve in a normally closed position operable by the variable depression of a button 138. In this embodiment, the valve 110 comprises a circular base 136 having a flat bottom surface and a pinch mechanism 140 configured to apply pressure to the tube 106 such that when the valve is in the closed position, flow of the sanitation fluid is prevented from passing through the valve 110. During use, as the button 138 is depressed, the valve opens proportionally enabling the user to control the rate the sanitation fluid is dispensed.

As best seen in FIG. 1, the valve 110 is configured to be installed and positioned on the arm band 104. In one embodiment, the flat bottom surface of the valve 110 includes a fastening member to facilitate the valve's attachment to the arm band 104. In some embodiments, the fastening member is a hook-and-loop fastening member. Advantageously, this allows the valve 110 to be repositioned for optimal use. For example, during use, the button 136 of the valve 110 is configured to be depressed between the medial aspect of the upper arm and the lateral aspect the chest wall (approximately in location 302; FIG. 1). Thus, giving the user the ability to position the valve 110 in the proper location is critical. Additionally, the valve 110 is configured to slide along the tube 106 in both a proximal and distal direction to further give the user the ability to correctly position the valve 110 during use.

As it is a particular object of the present invention to provide a non-contact, hands-free operated dispenser, being able to operable and depress the button 136 of the valve 110 without the use of hands provides a tremendous advantage over sanitation bottles and methods of the prior art, as the invention enables sanitation fluid to be dispensed at any time and any volume without requiring the user's hands. Moreover, user can control the fluid flow based on the amount of pressure exerted by the arm approximation movement to the chest wall.

Referring again to FIGS. 1-3, the tube 106 is of sufficient length to extend from the compressible pouch 130 inside the receptacle 102 to the user's hand. More particularly, the tube 106 is of sufficient length such that an outlet portion 108 of the tube 106 is positioned approximately to the user's palm. In some embodiments, straps 114 are provided to guide the tube 106 along the arm of the user such that the outlet 108 is in the intended position. In one embodiment, the straps 114 comprise a proximal strap and a distal strap, wherein the proximal strap is configured to fasten to a forearm of the arm, and the distal strap is configured to fasten to the wrist of the arm. However, it should be understood that the number, positions and sizes of the straps may vary. In some embodiments, clips 116 are attached to each strap 114, wherein the clips are configured to retain and secure the tube 106 to each strap 114. The clips and straps may attach in a variety of ways, including but not limited to, hook-and-loop fasteners, magnets, buttons, snaps, clips, or any type of fastener known in the art. In a preferred embodiment, magnets are used, as it is easy to install and remove the clips 116 from the straps 114. Further, if magnetic clips are used, it allows for the tube 106 to be released from the arm and straps if the tube 106 were to get caught or snapped on an object. Finally, the magnetic clip would permit the tube 106 can to be attached to the clip 116 over the long-sleeve shirt or a lab coat. Preferably, the clips 116 should be low-profile to avoid unintentionally hitting unintended surfaces. In one embodiment, the inner surface of each strap includes a non-stick silicon pad, wherein the straps, arm band, and receptacle are comprised of a fabric material. It should be understood, that any materials may be used.

In some embodiments, another clip can be placed on the strap 114 so the distal clip 116 and its attached tube 106 can be removed and attached (parked) into the strap 114. Such movement are necessary to remove the tube 106 when hand and forearm washing is desired, such as the case with surgical scrubbing.

As seen in FIG. 2, in some embodiments, the tube 106 may be comprised of multiple sections, having varied diameters, such as 106A and 106B. In other embodiments, the tube 106 is a single continuous tube of constant diameter. As user parameters change, the length of the tube can be customized for the specific user. Multiple sections offer the ability to adjust the length, such as telescoping tubes, or alternatively, the user may cut or trim the tube 106 to a desired length. Further, a smaller diameter tube 106B near the outlet 108 provides less material that may get in the way when the dispenser is not in use. Also, the varied diameter of the multiple sections changes the flow rate and dispensing characteristics as well known in the art. Advantageously, the elastic tube 106B allows for the portion near the outlet 108 to be moved out of the way when desired, such as rubbing hands together with the sanitation fluid, but the tube 106B is rigid enough to return to the intended position on approximate the palm of the user. In some embodiments, the smaller diameter tube 106B is curved configured to guide the outlet 108 portion of the tube into the palm of the user. In one embodiment, tube portion 106B is configured to telescope inside larger portion 106A, such that the length may vary as previously discussed.

In some embodiments, multiple slots 122 are provided for engagement with the arm strap 104 to accommodate different arm sizes. In one embodiment, a second opening 126 is provided to enable the tube 106 to enter the inner portion of the receptacle 102 such that it may be connected to the cap 132 of the compressible pouch 130 as previously discussed. The shape of the arm band and/or receptacle may vary, and may feature other structures outside of the scope of the invention, such as storage compartments.

Figure 5:
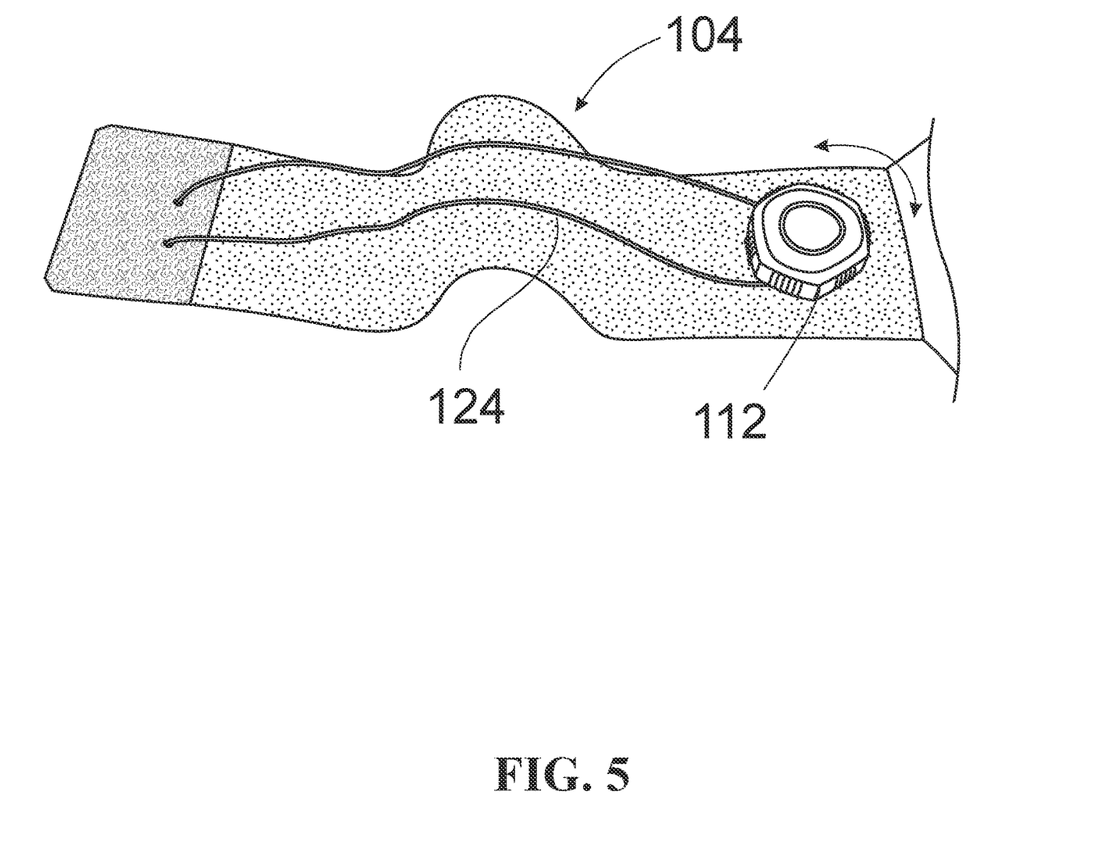

In some embodiments, tension wires 124 are provided and configured to compress the compressible pouch 130 during use. In one embodiment, the length of the tension wires is adjustable via a pressure adjustment knob 112. As seen in FIG. 5, as the knob 112 is rotated, it pulls the tensions wires 124 around the arm strap 104 such that when the dispenser is worn by the user, the tension wires compress the compressible pouch 130 within the receptacle's 102 housing where the pouch 130 is positioned during use. Similarly, the pressure may be released by rotating the knob 112 in the other direction. As previously mentioned, having a compressible pouch, bottle, or container is required for the embodiment discussed with the use of the tension wires 124 or alternative compression means. In some embodiments, the alternative compression means may include, but is not limited to an elastic crossing band with hook-and-loop fasteners, a compressing zipper configured to compress the compressible pouch 130 within the first opening 118, and a pneumatic pump configured to inflate a pouch integrated within the receptacle 102. In alternative embodiments, the sanitation fluid may be pre-pressurized, such that the sanitation fluid is configured to travel through the tube 106 without the need to compress the pouch, bottle, or container. For instance, a siphon may be used. In another embodiment, the sanitation fluid is pre-pressured with a pressure valve integrated in the nozzle of the pouch, wherein the valve can be released by a pin integrated within the cap. It should be understood that these are just a few examples, and one skilled in the art may realize various embodiments to move the sanitation fluid through the tube 106.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) are not used to show a serial or numerical limitation but instead are used to distinguish or identify the various members of the group.

Any element in a claim that does not explicitly state "means for" performing a specified function, or "step for" performing a specified function, is not to be interpreted as a "means" or "step" clause as specified in 35 U.S.C. § 112, ¶ 6. In particular, any use of "step of" in the claims is not intended to invoke the provision of 35 U.S.C. § 112, ¶ 6.

REFERENCE NUMBERS LIST

Receptacle 102
Arm Strap 104
Tube 106
First Tube Section 106A
Second Tube Section 106B
Tube Outlet 108
Valve 110
Pressure Adjustment Knob 112
Straps 114
Clips 116
First Opening 118
Zipper 120
Slots 122
Tension Wires 124
Second Opening 126
Compressible pouch 130
Cap 182
Valve Base 136
Valve Button 138
Valve Mechanism 140
O-Ring 142
Sanitation Liquid 200
User's Arm 300
Hands-free Valve Depression Location 302

What is claimed is:

1. A non-contact fluid dispenser comprising:
    a compressible container configured to hold a volume of fluid;
    a conduit having a first end and a second end, the first end in fluid communication with the volume of fluid, wherein the second end is in fluid communication with an outlet; and
    a valve configured to release fluid from the volume of fluid through the conduit, wherein the valve is operable without the use of a hand of a user;
    wherein the non-contact fluid dispenser is configured to be fastened to the user,
    wherein the valve includes a base and a button depressably connected to the base,
    wherein the base includes a pinch-type momentary control mechanism, said pinch-type momentary control mechanism being configured to apply pressure to the conduit when the button is not depressed such that the fluid is prevented from passing through the valve when the button is not depressed, and
    wherein a variable depression of the button is configured to open the valve proportionally to the depression to allow the fluid to pass through the valve,
    wherein the valve is configured to slide along the conduit in both a proximal and distal direction.

2. The dispenser of claim 1, wherein the volume of fluid is sanitation liquid configured to be dispensed into a hand of the user.

3. The dispenser of claim 1, wherein the compressible container is a disposable pouch.

4. The dispenser of claim 1, further comprising a receptacle having an inner volume, wherein the compressible container is removably housed in the inner volume of the receptacle.

5. The dispenser of claim 4, further comprising an arm strap configured to be fastened around an arm of the user, wherein the receptacle is attached to the arm strap.

6. The dispenser of claim 5, further comprising tension wires and a rotatable knob connected to the arm strap, wherein the rotatable knob is configured to pull the tension wires around the arm strap when being rotated, wherein the pulling of the tension wires is configured to apply pressure to the receptacle, and wherein the pressure applied to the receptacle due to the rotation of the rotatable knob is configured to compress the compressible container.

7. The dispenser of claim 1, wherein in a first mode of operation, the button of the valve is configured to be depressed between the medial aspect of an upper position on an arm and a lateral aspect of a chest wall of the user.

8. The dispenser of claim 1, wherein the conduit is a flexible elastic tube having an adjustable length.

9. The dispenser of claim 2, wherein the outlet is positioned approximately at a palm of the hand.

10. The dispenser of claim 9, further comprising at least one of: a forearm and wrist strap configured to hold and guide the conduit to the palm of the hand.

11. The dispenser of claim 1, wherein the compressible container includes a leak-proof cap, wherein the first end of the conduit is received by the cap.

12. The dispenser of claim 4, wherein the receptacle has a first opening enabling the removal of the compressible container such that a new compressible container may be installed, wherein the first opening is reversibly closable via a fastener.

13. The dispenser of claim 12, wherein the receptacle has a second opening configured to enable the conduit to enter the inner volume of the receptacle.

14. A wearable non-contact fluid dispenser comprising:
    an arm band and a compressible receptacle attached to the arm band, wherein the arm band is configured to be fastened to a user's arm;
    a compressible pouch configured to hold a volume of sanitation fluid housed in the compressible receptacle;
    a flexible elastic tube having a first end and a second end, the first end is in fluid communication with the volume of sanitation fluid, wherein the second end forms an outlet, and the outlet is positioned approximately to the user's palm;
    a valve connected to the flexible elastic tube, wherein the valve is configured to enable the sanitation fluid to flow from the compressible pouch, through the flexible elastic tube and into the user's palm in response to being compressed by the user, wherein the valve is compressible by the user without utilizing the user's hands; and
    tension wires and a rotatable knob connected to the arm band, wherein the rotatable knob is configured to pull the tension wires around the arm band when being rotated, wherein the pulling of the tension wires is configured to apply pressure to the receptacle, and wherein the pressure applied to the receptacle due to the rotation of the rotatable knob is configured to compress the compressible container, wherein the valve includes a base and a button depressably connected to the base, wherein the base includes a pinch-type momentary control mechanism, said pinch-type momentary control mechanism being configured to apply pressure to the flexible elastic tube when the button is not depressed such that the fluid is prevented from passing through the valve when the button is not depressed, wherein a variable depression of the button is configured to open the valve proportionally to the depression to allow the fluid to pass through the valve, and wherein the valve is configured to slide along the flexible elastic tube in both a proximal and distal direction.

15. A non-contact fluid dispenser comprising: a compressible container configured to hold a volume of fluid; a conduit having a first end and a second end, the first end in fluid communication with the volume of fluid, wherein the second end is in fluid communication with an outlet; a valve configured to release fluid from the volume of fluid through the conduit, wherein the valve is operable without the use of a hand of a user; an arm strap configured to be fastened around an arm of the user, wherein a receptacle is attached to the arm strap, and tension wires and a rotatable knob connected to the arm strap, wherein the rotatable knob is configured to pull the tension wires around the armstrap when being rotated, wherein the pulling of the tension wires is configured to apply pressure to the receptacle, and wherein the pressure applied to the receptacle due to the rotation of the rotatable knob is configured to compress the compressible container, wherein the non-contact fluid dispenser is configured to be fastened to the user, wherein the valve includes a base and a button depressably connected to the base, wherein the base includes a pinch-type momentary control mechanism, said pinch-type momentary control mechanism being configured to apply pressure to the conduit when the button is not depressed such that the fluid is prevented from passing through the valve when the button is not depressed, and wherein a variable depression of the button is configured to open the valve proportionally to the depression to allow the fluid to pass through the valve.

\* \* \* \* \*